(12) United States Patent
Avery

(10) Patent No.: US 9,833,590 B2
(45) Date of Patent: Dec. 5, 2017

(54) STERILIZATION AND HUMIDIFICATION APPARATUS AND INCUBATOR

(71) Applicant: Mondiale Technologies Limited, Auckland (NZ)

(72) Inventor: Raymond John Avery, Auckland (NZ)

(73) Assignee: Mondiale Technologies Limited, Auckland (NZ)

( * ) Notice: Subject to any disclaimer, the term of this patent is extended or adjusted under 35 U.S.C. 154(b) by 378 days.

(21) Appl. No.: 14/383,088

(22) PCT Filed: Mar. 1, 2013

(86) PCT No.: PCT/NZ2013/000028
§ 371 (c)(1),
(2) Date: Sep. 4, 2014

(87) PCT Pub. No.: WO2013/133722
PCT Pub. Date: Sep. 12, 2013

(65) Prior Publication Data
US 2015/0031939 A1   Jan. 29, 2015

(30) Foreign Application Priority Data

Mar. 6, 2012 (NZ) ........................ 598597

(51) Int. Cl.
*A61G 11/00* (2006.01)
*A61M 16/16* (2006.01)
(Continued)

(52) U.S. Cl.
CPC ........... *A61M 16/161* (2014.02); *A61G 11/00* (2013.01); *A61M 16/107* (2014.02);
(Continued)

(58) Field of Classification Search
CPC ...... A61G 11/00; A61G 10/04; A61G 11/005; A61G 2203/46; A61M 16/16
See application file for complete search history.

(56) References Cited

U.S. PATENT DOCUMENTS 2,066,271 A   12/1936   Irwin
3,821,947 A * 7/1974   Schossow .............. A61G 11/00
                                                    128/203.27
(Continued)

FOREIGN PATENT DOCUMENTS

WO   WO-98/16263   4/1998
WO   WO-2009/042264   4/2009
(Continued)

OTHER PUBLICATIONS

International Preliminary Report on Patentability in PCT/NZ2013/000028 dated Sep. 9, 2014. 12 pages.

*Primary Examiner* — Christine H Matthews
(74) *Attorney, Agent, or Firm* — Thomas Coester Intellectual Property

(57) ABSTRACT

A sterilization and humidification apparatus includes a heating chamber, a filter and a humidification chamber. The heating chamber heats a gas so as to sterilize the gas. The humidification chamber is adapted so that a liquid, which has been filtered by the filter, evaporates into the sterilized gas, thereby causing the sterilized gas to cool, and outputting a humidified gas at a desired temperature. The apparatus may include a bypass chamber to provide a path for the gas to bypass the humidification chamber. The apparatus may be adapted particularly for use in an incubator.

18 Claims, 13 Drawing Sheets

(51) Int. Cl.
*A61M 16/10* (2006.01)
*F24F 6/02* (2006.01)
*F24F 6/00* (2006.01)

(52) U.S. Cl.
CPC ........ *A61M 16/108* (2014.02); *A61M 16/109* (2014.02); *A61M 16/16* (2013.01); *F24F 6/02* (2013.01); *A61G 11/005* (2013.01); *A61G 2203/46* (2013.01); *A61M 2205/3368* (2013.01); *A61M 2205/3386* (2013.01); *A61M 2205/3653* (2013.01); *A61M 2230/04* (2013.01); *A61M 2230/50* (2013.01); *A61M 2240/00* (2013.01); *F24F 2006/006* (2013.01)

(56) References Cited

U.S. PATENT DOCUMENTS

| | | | |
|---|---|---|---|
| 4,280,658 A | 7/1981 | Ehrrich | |
| 4,940,475 A | 7/1990 | Jaeger | |
| 6,878,177 B2 * | 4/2005 | Lohr | B01D 46/0024 219/407 |
| 2004/0133064 A1 * | 7/2004 | Castillon Levano | A61G 11/00 600/22 |
| 2009/0223514 A1 | 9/2009 | Smith et al. | |
| 2010/0242961 A1 | 9/2010 | Mougel et al. | |
| 2012/0006324 A1 | 1/2012 | Nichols et al. | |

FOREIGN PATENT DOCUMENTS

| | | |
|---|---|---|
| WO | WO-2011/014540 | 2/2011 |
| WO | WO-2011/031167 | 3/2011 |

* cited by examiner

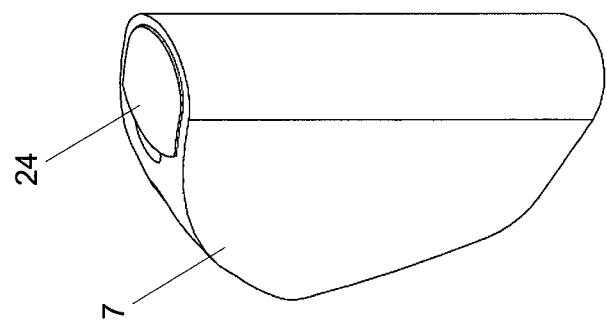
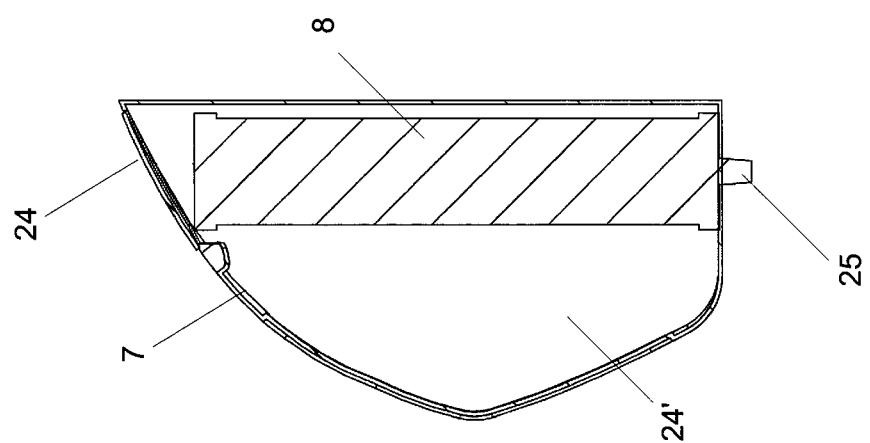

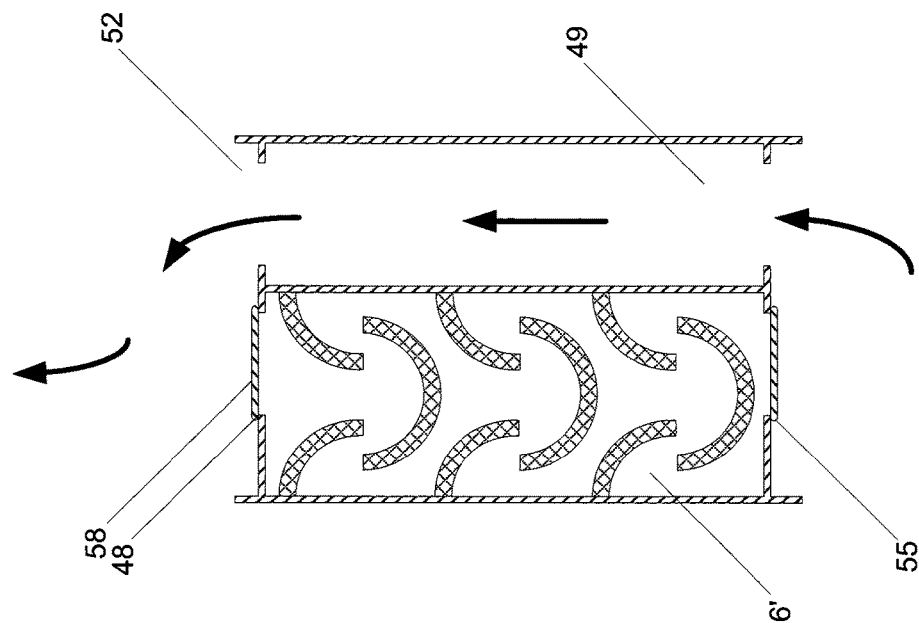
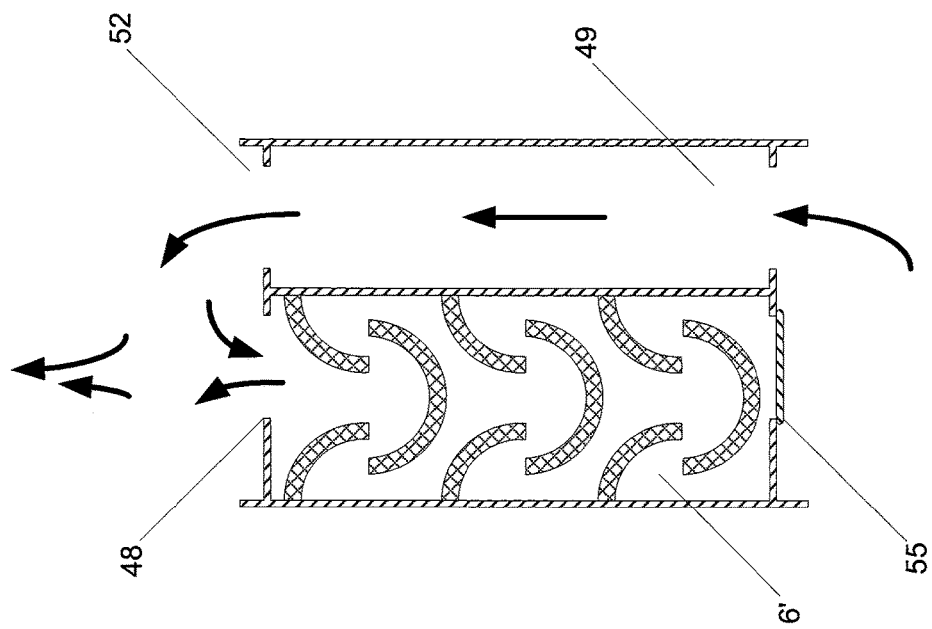

STERILIZATION AND HUMIDIFICATION APPARATUS AND INCUBATOR

FIELD OF THE INVENTION

The invention relates to sterilization and humidification apparatuses, in particular but not exclusively to incubators including sterilization and humidification apparatuses.

BACKGROUND TO THE INVENTION

Premature and unwell babies are often cared for in incubators, which are designed to keep the baby warm, maintain an atmosphere that has a suitable humidity and that is as free of contaminants as possible.

Existing incubators may include systems designed to introduce clean air into the main chamber of the incubator. Such air should ideally be as free as possible of particulate and microbial contaminants. In some hospital environments, the ambient air is already sufficiently clean (due to, for example, air conditioning systems) such that incubators do not necessarily need specialised air treatment equipment. However, in other hospital environments—particularly in developing countries—the ambient air has undergone minimal conditioning, and therefore the need for specialised air treatment in incubators is of more importance.

In addition to clean air, existing incubators include systems designed to provide a suitably humidified environment inside the main chamber of the incubator. The water used in humidification systems should ideally be as free as possible of particulate and microbial contaminants. In some hospitals—particularly in developing countries—a clean water source is often not available, and therefore the need for specialised water treatment in incubators is of more importance.

Current incubators suffer from a number of problems. Incubators tend to be made of expensive materials and require regular maintenance. This serves to increase the costs and make the incubators less affordable and accessible. This is particularly the case in developing countries.

Maintenance of existing incubators can also be expensive. In developing countries there is sometimes no one who has the expertise necessary to perform even routine maintenance tasks. This leads to expensive incubators being unusable because of routine faults and lack of scheduled preventative maintenance.

As discussed earlier, there are systems available which attempt to maintain a sterilized environment, but such systems are often expensive, bulky and require regular servicing or replacement.

It is an object of the invention to provide an improved sterilization and humidification apparatus and/or an improved incubator or at least to provide the public with a useful choice.

SUMMARY OF THE INVENTION

According to one exemplary embodiment there is provided a sterilization and humidification apparatus including: a heating chamber for heating a gas to a first temperature so as to sterilize the gas; a first filter for filtering a liquid; and a humidification and cooling chamber adapted to enable the filtered liquid to evaporate into the sterilized gas, thereby causing the sterilized gas to cool, and outputting a humidified gas at a desired temperature.

According to another exemplary embodiment there is provided an incubator including: a sterilization and humidification apparatus as claimed in any preceding claim; and an occupancy chamber; wherein the incubator is adapted to cause the humidified gas to flow into the occupancy chamber.

According to a further exemplary embodiment there is provided an incubator including: an occupancy chamber; a first inlet for receiving an input gas; a second inlet for receiving an input liquid; and a porous ceramic filter for filtering the input liquid; wherein the incubator is configured to evaporate the input liquid into the input gas after the input liquid has passed through the porous ceramic filter, thereby producing a humidified gas, which is made to flow into the occupancy chamber.

BRIEF DESCRIPTION OF THE DRAWINGS

The invention will now be described by way of example only, with reference to the accompanying drawings, in which:

FIG. 6a is a cross section of a liquid source and a liquid filter of the sterilization and humidification apparatus of FIG. 2;

FIG. 6b is an isometric view of a liquid source and a liquid filter of the sterilization and humidification apparatus of FIG. 2;

FIGS. 10a and 10b is a cross section of the humidification and cooling chamber and bypass chamber of the sterilization and humidification apparatus of FIG. 8;

DETAILED DESCRIPTION

Figure 1:
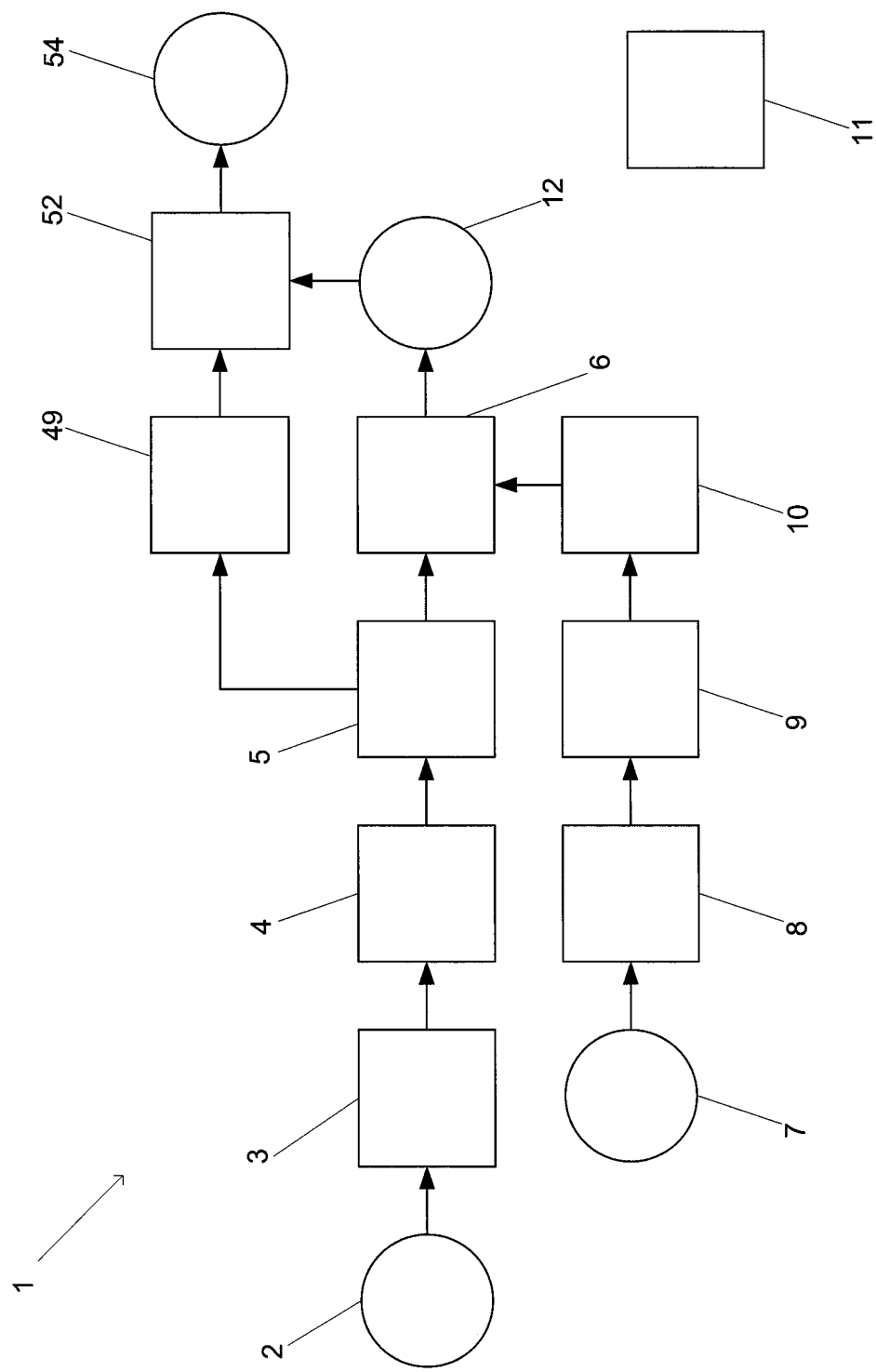
FIG. 1 is a block diagram of a sterilization and humidification apparatus according to the present invention.

FIG. 1 is a block diagram of a sterilization and humidification apparatus 1 according to one embodiment. Generally, the sterilization and humidification apparatus may include a gas source (later referred to as an 'air source') 2, a gas filter (later referred to as an 'air filter') 3, a flow device 4 (e.g. a fan), a heating chamber 5, a humidification and cooling chamber 6, a liquid source (later referred to as a 'water source') 7, a liquid filter (later referred to as a 'water filter') 8, a reservoir 9, a wicking member 10 and a controller 11. In some embodiments, the humidification chamber 6 may act as a humidification and cooling chamber.

Figure 2:
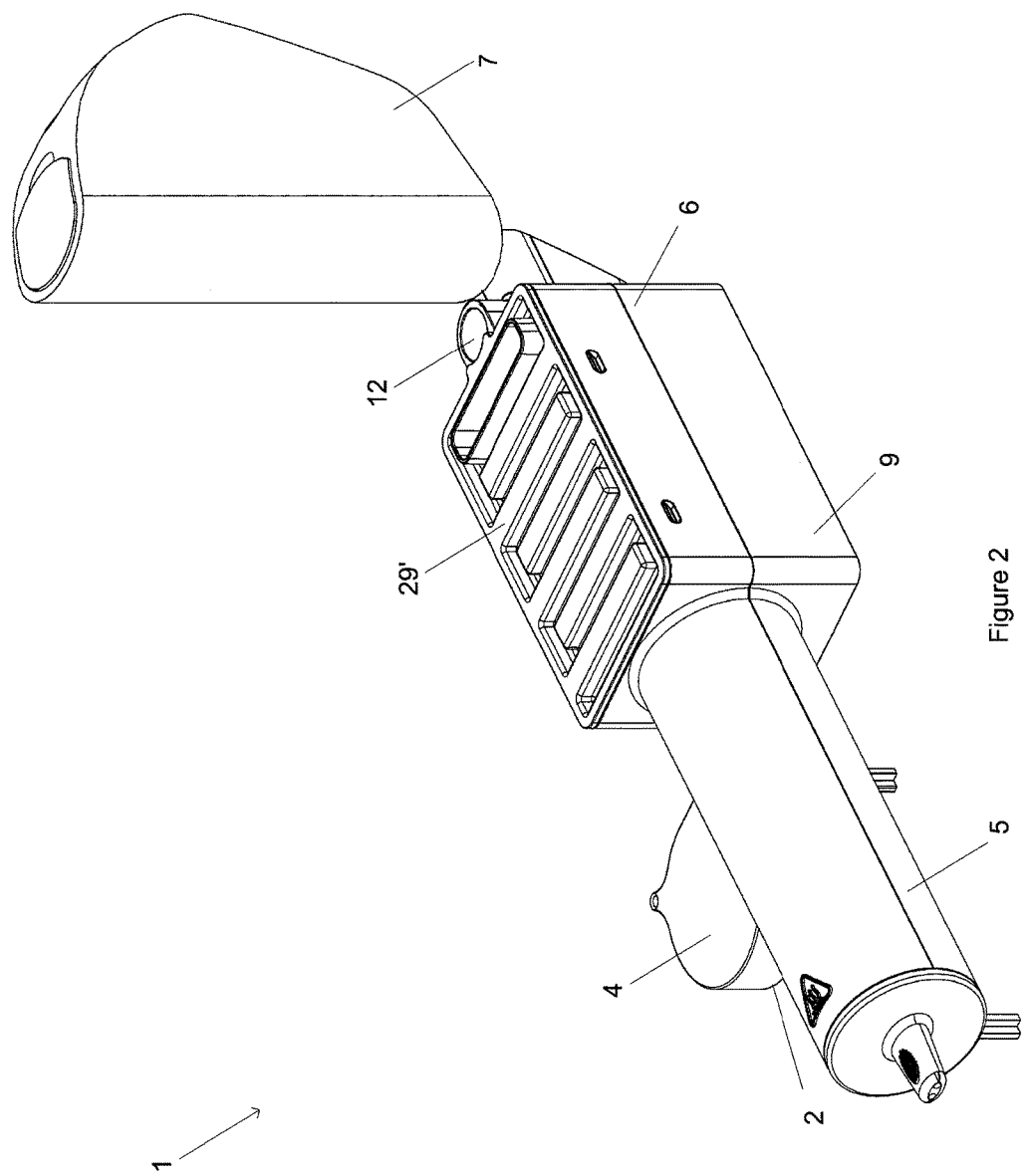
FIG. 2 is an isometric view of an assembled sterilization and humidification apparatus.

FIG. 2 shows an assembled sterilization and humidification apparatus 1 according to one embodiment. The figure shows a flow device 4, a heating chamber 5, a humidification chamber 6, a reservoir 9 and a water source 7. Other components of the sterilization and humidification apparatus are obscured. Gas and liquid flow through the sterilization and humidification apparatus 1 according to the description of each step and component part outlined below.

Those skilled in the art will appreciate that in some instances it is necessary for the steps to happen sequentially or in a particular order, and in other instances the sequence of the step is not critical. As will become apparent from the description, the operation of the sterilization and humidification apparatus results in the output of a humidified gas 12 (FIG. 1), with the constituent gas and liquid both having been filtered and/or sterilized. In some embodiments, the sterilization and humidification apparatus may also include a bypass chamber 49 and a mixing chamber 52, resulting in the output of a mixed humidified gas 54, as discussed below.

The sterilization and humidification apparatus 1 is connected to a gas source 2. In a preferred embodiment, the gas is air. There are any number of suitable ways by which air can be introduced into an apparatus. By way of example, air from the ambient environment may enter the sterilization and humidification apparatus through a basic inlet; or a pressurised air source may be connected to the sterilization and humidification apparatus by a suitable conduit. Any suitable fan or similar may be used to introduce air.

The sterilization and humidification apparatus 1 is also connected to a liquid source 7. In a preferred embodiment, the liquid is water. There are any number of suitable ways by which water can be introduced into an apparatus. By way of example, the water source could be a tank that is manually filled or replaced, which can be connected to the sterilization and humidification apparatus by a suitable conduit; or the water source could be a pressurised water source (such as the water mains) which can be connected to the sterilization and humidification apparatus by a suitable conduit.

Figure 3:
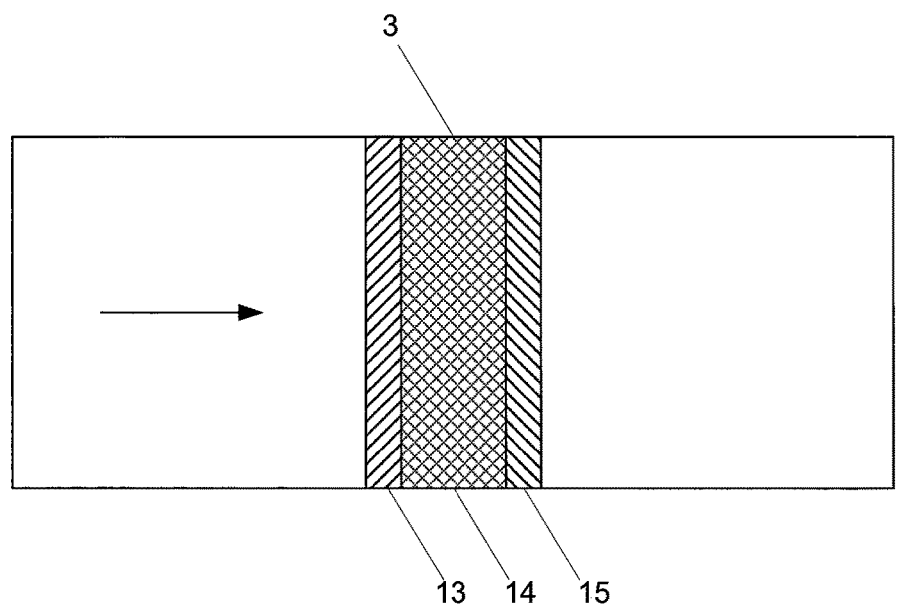
FIG. 3 is a cross section of a gas filter.

FIG. 3 shows an air filter 3. The air, after entering the sterilization and humidification apparatus, flows through the air filter as indicated by the arrow. The air filter serves to remove particulate contaminants from the air. It will be appreciated that the air filter should ideally be disposed such that it interrupts the entire flow of air through the sterilization and humidification apparatus. In one embodiment, the air filter is made up of a plurality of filter media 13, 14, 15 ordered sequentially in the flow of air. In one embodiment, the main filter 14 is a High Efficiency Particle Arresting (HEPA) filter which has a particle arrestance of 95-99.7% for 0.3-0.5 micron particles.

The air filter 3 may include a readily replaceable pre-filter 13 disposed on the air filter's upstream side. The pre-filter may be readily removed, washed and replaced. Such a pre-filter serves to extend the lifespan of the other components of the air filter 14, 15. The pre-filter may be made of a polypropylene or other suitable material.

The air filter 3 may also include a filter material 15 impregnated with nanoparticulate silver on its downstream side. This helps to prevent the propagation of microbial contamination on the downstream side of the HEPA filter 14 (ie contributes to the sterilization of the air).

Figure 4:
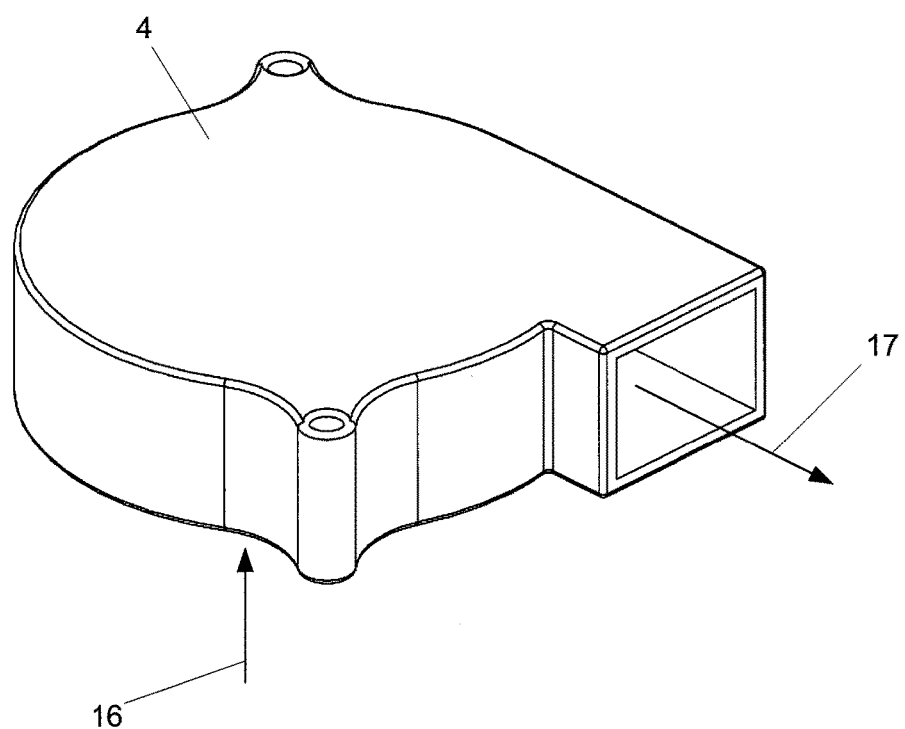
FIG. 4 is an isometric view of a flow device.

FIG. 4 shows a flow device 4 according to one embodiment. The flow device may include a fan (not shown), which draws in air in one direction 16, and expels air in another direction 17. Such a flow device is configured so as to ensure the air flows through the sterilization and humidification apparatus at the desired speed and pressure. As will be described later, the flow device may be connected to a controller which controls the operation of the flow device, including the speed of the fan. The flow device may be upstream or downstream of the air filter 3. In another embodiment, the flow device may be a pump.

Figure 5:
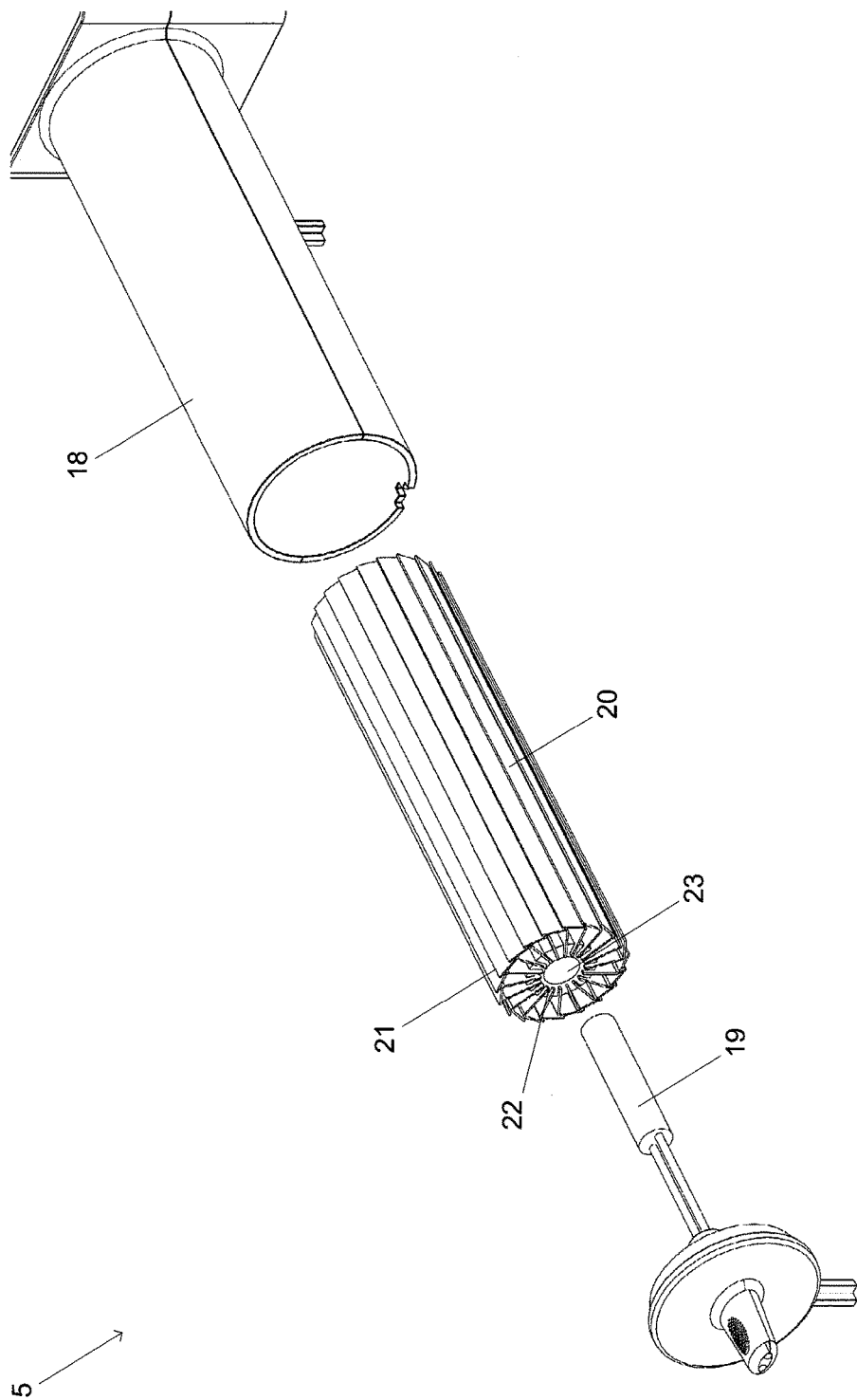
FIG. 5 is an exploded view of a heating chamber of the sterilization and humidification apparatus of FIG. 2.

FIG. 5 shows an exploded view of a heating chamber according to one embodiment of the present invention. The heating chamber includes a housing 18, a heater element 19 and a conducting bulk material 20, which in FIG. 5 is shown as series of fins 21 embedded radially in a cylindrical base member 22. The heater element and conducting bulk material are adapted so that the conducting bulk material dissipates heat from the heater element. The cylindrical base member may include a hollow core 23 that receives the heater element inside it.

The heater element 19 may be any suitable device that can be connected to a power source (not shown) and generate heat. In a preferred embodiment, the base member 22 and fins 21 are made predominately from a conductive material, such that when the heater element is switched on, heat is conducted from the heater element, to the base member, and to the fins. The air enters the heating chamber 5 through an inlet (not shown) adjacent to the flow device. The air then flows adjacent or near the radial extremities of the fins in an outer region of the heating chamber between the fins and the inside of the housing 18 (to the left as shown in FIG. 5). The air passes around the end of the bulk material 20, into an inner region between the base member 22 and fins. The air then flows along the length of the bulk material 20 (to the right as shown in FIG. 5), before exiting the heating chamber through an outlet (not shown).

As will be appreciated by those skilled in the art, the arrangement of the heater element 19 and conducting bulk material 22 are such as to maximise the exposure of the air to the conducting bulk material as the air flows through the heating chamber 5. This increases the effectiveness of the heating of the air in the heating chamber. Typically, this can be achieved by configuring the heating chamber with an air flow (ie the course that the air must follow) that increases the exposure of the air to heat and lengthens the path between the inlet and outlet. In addition to the conductive bulk material, the heating chamber may also include suitable protrusions to direct the flow of the air as it passes through the heating chamber.

Thus, the air will increase in temperature as it passes through the heating chamber 5. The temperature should be sufficient to sterilize the air. In a preferred embodiment, the air is heated to 180-200 degrees Celsius. As will be described later, the heating chamber may include temperature sensors to ensure that the air is being heated to a sufficiently high temperature. The heater element 19 may be connected to a controller for control of heating power.

FIG. 6a shows a cross section of a water source 7 and a water filter 8, and FIG. 6b shows an isometric view of the exterior of the water source 7. The water source is a tank that can be manually filled through an opening 24. Disposed inside the water tank is a cylindrical water filter 8. The top of the water filter is closed so water flows initially into the tank space 24'. Water passes from the water tank into the water filter, and out an outlet 25. Preferably, the water filter is a ceramic filter with a porous ceramic body structure. The maximum pore size of the porous ceramic is preferably 0.1-0.2 microns, and ideally 0.2 microns. In this way, the water that flows our of the water filter and into the remainder of the sterilization and humidification apparatus is filtered water.

In a further embodiment, the porous ceramic of the water filter 8 is impregnated with nanoparticulate silver. Nanoparticulate silver has antibacterial properties and therefore, as the water passes through the water filter, the water is also sterilized. In addition to, or alternatively to, the nanoparticulate silver, the water filter may be configured with a hollow core that is filled with silvered quartz pieces. The dimension of the pieces may be 2-5 mm in diameter. Again, the silvered quartz pieces have an antibacterial effect on the water that flows adjacent or near to it, and this causes the water to be sterilized.

Figure 7:
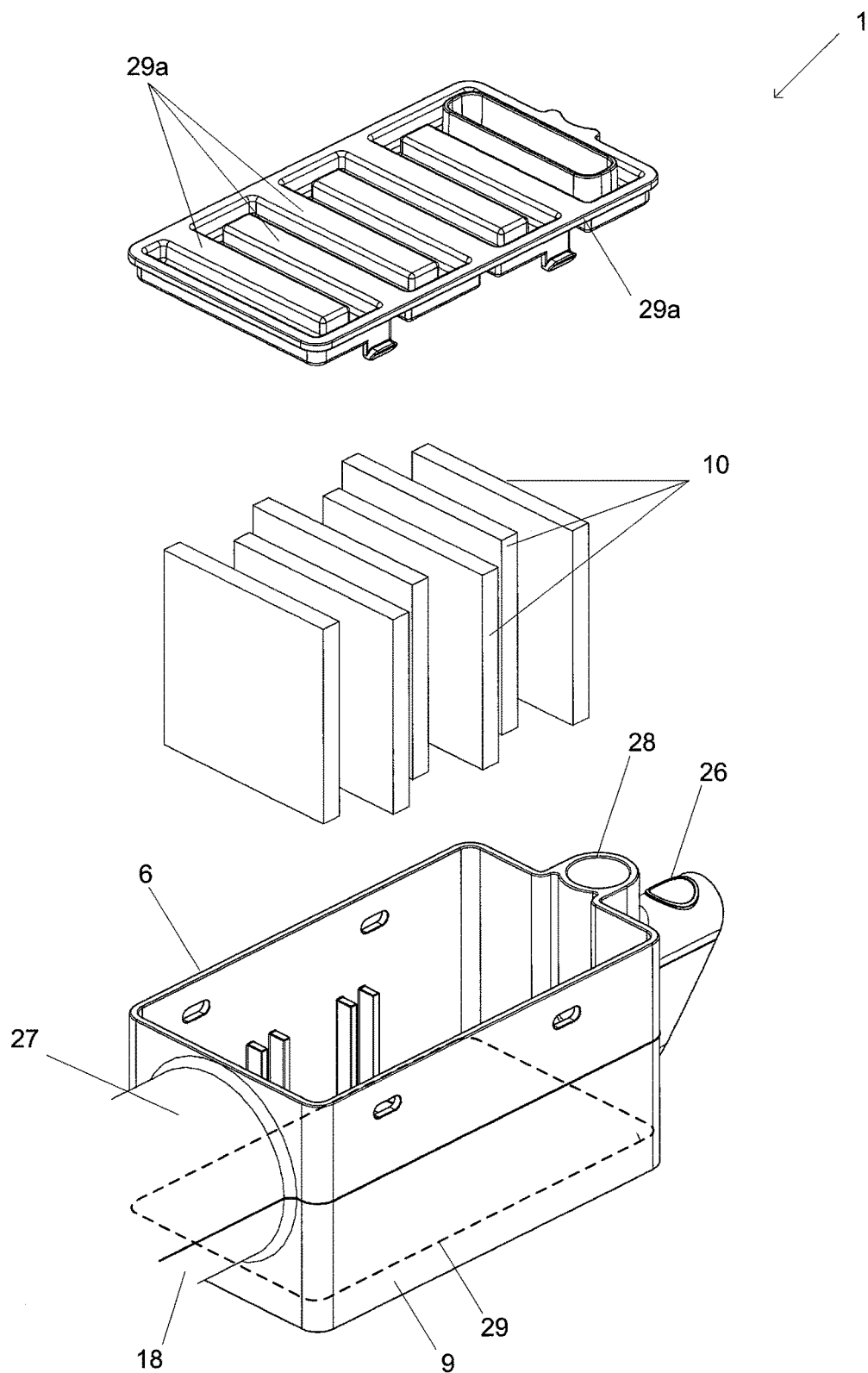
FIG. 7 is an exploded view of a reservoir, wicking members and a humidification and cooling chamber of the sterilization and humidification apparatus of FIG. 2.

FIG. 7 shows an exploded view of part of the sterilization and humidification apparatus 1. A reservoir 9 is obscured—being the region below the dotted line 29. FIG. 7 also shows wicking members 10 (three of which are indicated), a humidification and cooling chamber 6, and a cap 29a which together are configured as a single unit. FIG. 7 also shows a portion of the housing 18 from FIG. 5.

The reservoir 9 includes an inlet 26 that is suitably connected to the outlet 25 from the water source 7/water filter 8. The reservoir 9 is configured so that it has a continuous supply of water. In this instance, the water source 7 described earlier is disposed higher than the reservoir in such a way that provided the water tank is kept sufficiently full, the amount of water in the reservoir is always sufficient.

The humidification and cooling chamber 6 includes an inlet 27 that is connected to the outlet from the heating chamber. Through this inlet, the heated air from the heating chamber enters the humidification and cooling chamber. As will be described in more detail below, as the heated air passes through the humidification and cooling chamber it is humidified and cooled. The humidification and cooling chamber also includes an outlet 28, from which the humidified air exits the sterilization and humidification apparatus.

Between the reservoir and the humidification and cooling chamber, there is a barrier (as shown by the dotted line 29) through which the wicking members 10 are positioned. The barrier and wicking members are arranged such that there is no direct interface between the water in the reservoir 9 and the air in the humidification and cooling chamber 6. The wicking members are configured such that a portion of each wicking member is always in contact with the water in the reservoir and a portion of each wicking member is always in contact with the air in the humidification and cooling chamber.

Each wicking member 10 is adapted to draw water from the reservoir 9 by capillary action, and thus the water is able to traverse the barrier 29 between the reservoir and the humidification and cooling chamber 6. The wicking members may be disposed in a vertical arrangement with the reservoir on the bottom, and thus the capillary action acts against gravitational force.

In one embodiment, the wicking members 10 are made from a porous ceramic and act as a filter in addition to a wick. The maximum pore size of the porous ceramic is preferably 0.1-0.2 microns, and ideally 0.2 microns. In this way, the water that flows from the reservoir to the humidification and cooling chamber is filtered.

In a further embodiment, the porous ceramic of the wicking members 10 is impregnated with nanoparticulate silver. As the water passes through the wicking members, the water is also sterilized.

The portion of the wicking member 10 in contact with the heated air acts as an evaporative surface, from which the water evaporates into the heated air. The positioning of the wicking members in the humidification and cooling chamber 6 is such as to increase the exposure of the heated air to the evaporative surface of the wicking members. In one embodiment, the wicking members define the boundary of a meandering course in the humidification and cooling chamber through which the heated air flows. The cap 29a helps to maintain the wicking members in position (with shaped regions 29b receiving the tops of the wicking members 10) and also seals the top of the humidification and cooling chamber.

Once the water has flowed to the evaporative surface, it then evaporates into the heated air. As the water evaporates into the heated air, the heated air becomes humidified. Further, the heated air cools as it loses energy due to the latent heat of vaporization needed to change the phase of the water from a liquid to a gas (i.e. steam or water vapour).

In an alternative embodiment that will be described below, the proportion of the heated air that passes through the humidification and cooling chamber may be adjusted to control the temperature and humidity of the humidified air exiting the humidification and cooling chamber. As will also be described below, adjusting the temperature of the heating chamber and the speed of the flow device may also allow the temperature and humidity of the humidified air to be controlled.

Figure 8:
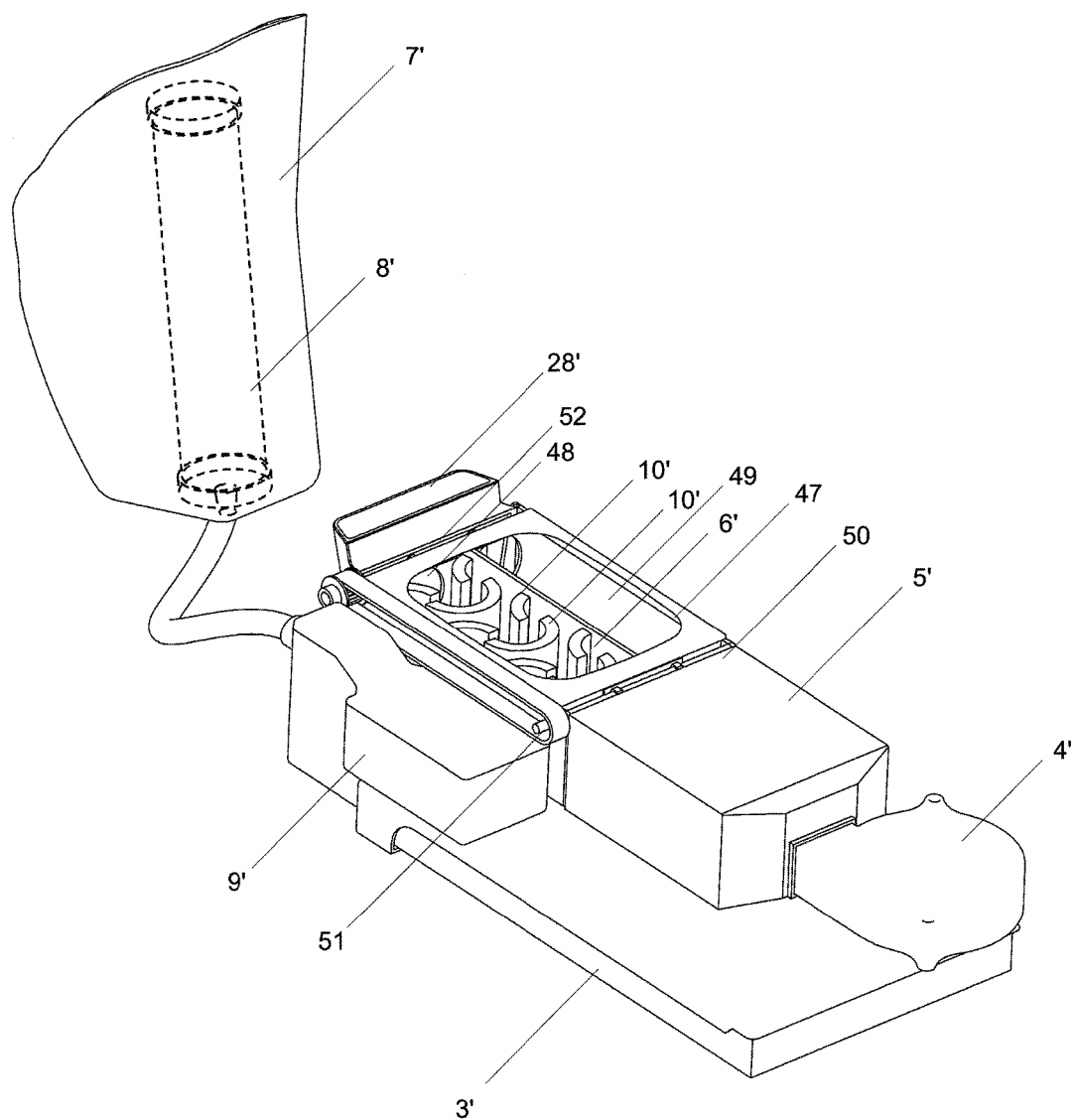
FIG. 8 is an isometric view of an assembled sterilization and humidification apparatus according to another embodiment.

FIG. 8 shows another embodiment of a sterilization and humidification apparatus 1'. In this embodiment, the proportion of heated air that passes through the humidification and cooling chamber can be controlled, which in turn allows the temperature and humidity of the humidified air to be controlled.

As with the embodiment described above in relation to FIGS. 2-7, the sterilization and humidification apparatus 1' of FIG. 8 includes an air filter 3', a flow device 4', a heating chamber 5', a humidification and cooling chamber 6', a water source 7', a water filter 8', a reservoir 9' and wicking members 10' (two of which have been indicated). The humidification and cooling chamber may include a transparent top window 47 to enable easy inspection. The flow device causes air to flow through the air filter to filter contaminates. The air then flows through the heating chamber, heating to a sufficient temperature to sterilize the air, before it flows into the humidification and cooling chamber. Water from the water source is filtered and/or sterilized before collecting in the reservoir. The wicking members cause the water from the reservoir to be drawn up into the humidification and cooling chamber. The wicking members may filter and/or sterilize the water. The heated air causes the water to evaporate from the wicking members; this humidifies and cools the heated air to produce humidified air, which then exits the humidification and cooling chamber from a humidification and cooling chamber outlet 48. Those skilled in the art will appreciate how the various features described in relation to the apparatus of FIGS. 2-7 can be modified to apply to the apparatus of FIGS. 8 and 9.

Figure 9:
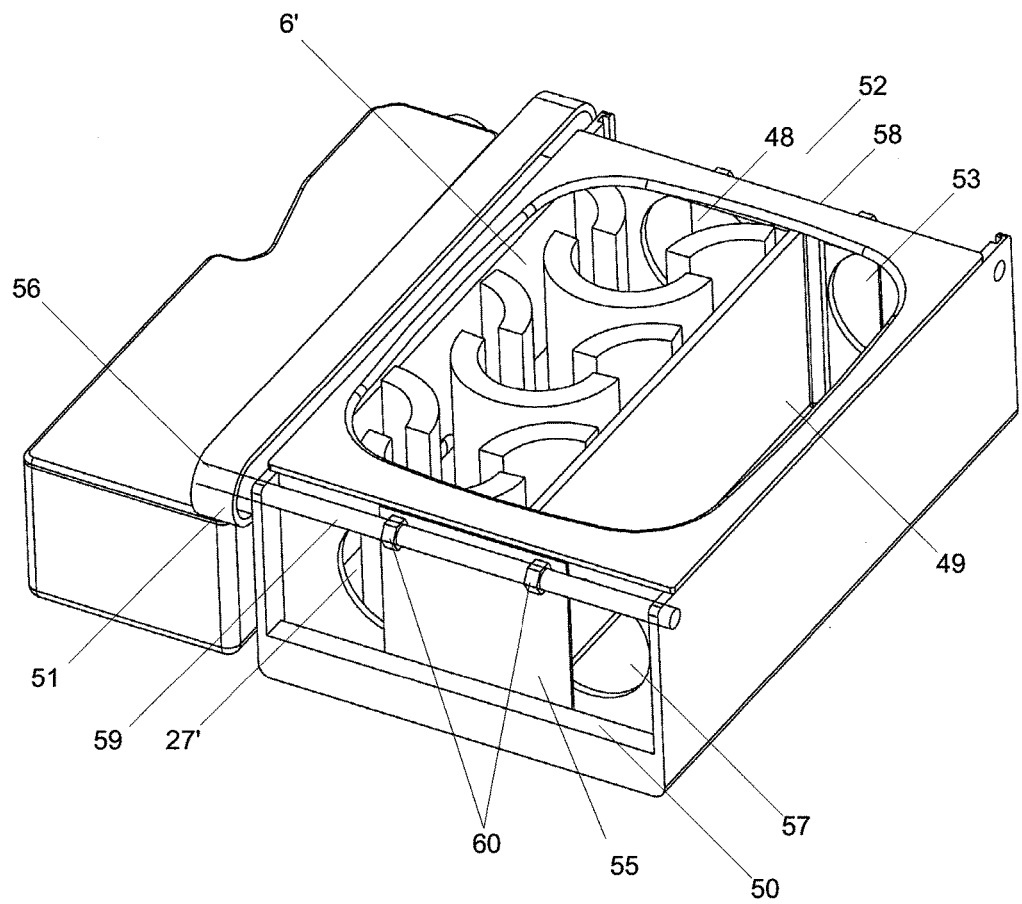
FIG. 9 is an isometric view of a portion of the sterilization and humidification apparatus of FIG. 8.

However, unlike the apparatus of FIGS. 2-7, the sterilization and humidification apparatus of FIG. 8 also includes a bypass chamber 49, distribution chamber 50, a distribution adjustment mechanism 51 and a mixing chamber 52 as shown in FIG. 8 and in the partial view of the apparatus in FIG. 9. It will be appreciated that the distribution chamber and mixing chamber are not shown as enclosed volumes in FIG. 9 since parts of the apparatus have been removed to show the interior more clearly.

The bypass chamber 49 provides an alternative path for a portion of the heated air flowing out of the heating chamber. Rather than flow through the humidification and cooling chamber 6', some of the heated air may flow through the bypass chamber. In the bypass chamber, the heated air is not exposed to any water, and therefore the heated air exits the bypass chamber through a bypass chamber outlet 53 with essentially the same temperature and humidity as when it entered the bypass chamber. The heated air that exits through the bypass outlet then mixes with the humidified air that exits through the humidification and cooling chamber outlet 48 in the mixing chamber 52. The mixed humidified air (i.e. humidified and heated air, and heated air), then exits the apparatus through an apparatus outlet (28' in FIG. 8).

The distribution chamber 50 connects the heating device 5' to the humidification and cooling chamber 6' and the bypass chamber 49. By adjusting a suitable distribution adjustment mechanism 51, it is possible to control what proportion of heated air flows into the humidification and cooling chamber and what proportion of the heated air flows into the bypass chamber. It will be appreciated that by increasing the proportion of heated air that flows into the bypass chamber, the mixed humidified air will have a higher temperature and lower humidity. Conversely, by decreasing the proportion of heated air that flows into the bypass chamber, the mixed humidified air will have a lower temperature and higher humidity.

Thus, by adjusting the distribution adjustment mechanism the temperature and humidity of the mixed humidified air can be regulated. In one embodiment, after the apparatus is operating at a set air speed and rate of heating, the temperature and humidity of the humidified air can be further regulated by adjusting the distribution adjustment mechanism.

In FIG. 9, the distribution adjustment mechanism 51 is shown as an inlet sliding valve 55 connected to a suitable drive mechanism 56. The inlet sliding valve is configured to slide between: a first position that fully seals the humidification and cooling chamber inlet 27', a second position that fully seals the bypass chamber inlet 57; and a range of positions between the first position and second position where both inlets are partially open. The inlet sliding valve is therefore able to fully or partially block the passage of the heated air into and through each of the humidification and cooling chamber 6' and the bypass chamber 49. With the inlet sliding valve in the first position, all of the heated air flows through the bypass chamber, and with the sliding valve in the second position, all of the heated air flows through the humidification and cooling chamber.

In one embodiment, the distribution adjustment mechanism 51 may include a further outlet sliding valve 58 (obscured) that is configured to slide between: a first position that fully seals the humidification and cooling chamber outlet 48, a second position that fully seals the bypass chamber outlet 53; and a range of positions between the first position and second position where both outlets are partially open. In a preferred embodiment, the inlet sliding valve and outlet sliding valve 55 may be slid between their first and second positions in unison. The sliding valves may be connected to the same drive mechanism 56.

The benefit of having both an inlet valve 55 and an outlet valve 58 is best shown by considering an apparatus that only has an inlet sliding valve (as shown in the cross-section of FIG. 10*a*). If the inlet sliding valve is in the first position, all of the heated air flows through the bypass chamber 49. As the heated air passes through the mixing chamber 52, the venturi effect causes some of the heated air to flow into and out of the humidification and cooling chamber 6' via the humidification and cooling chamber outlet 48. This may result in some humidified air being mixed with the heated air. Conversely, if there is also an outlet sliding valve 58 (as shown in the cross-section of FIG. 10*b*), there is no opportunity for the venturi effect to occur, and thus there is no unwanted increase in humidity. This allows a less humid and warmer air to be output. It will be appreciated how the above reasoning can also apply to the situation where the sliding valve is in the second position, which allows a more humid and cooler air to be output. Therefore, having two sliding valves allows air with a greater range of humidity and temperature to be output and with more precision.

The drive mechanism 56 may be a screw driven stepping motor or a suitable manually adjustable mechanical drive mechanism. The drive mechanism may be connected to a controller. The controller may automatically control the drive mechanism based on data from sensors so that the mixed humidified air has the desired temperature and humidity. The mechanism may include a rotating threaded shaft 59 riding in fixed nuts 60 attached to the sliding valve.

Figure 11:
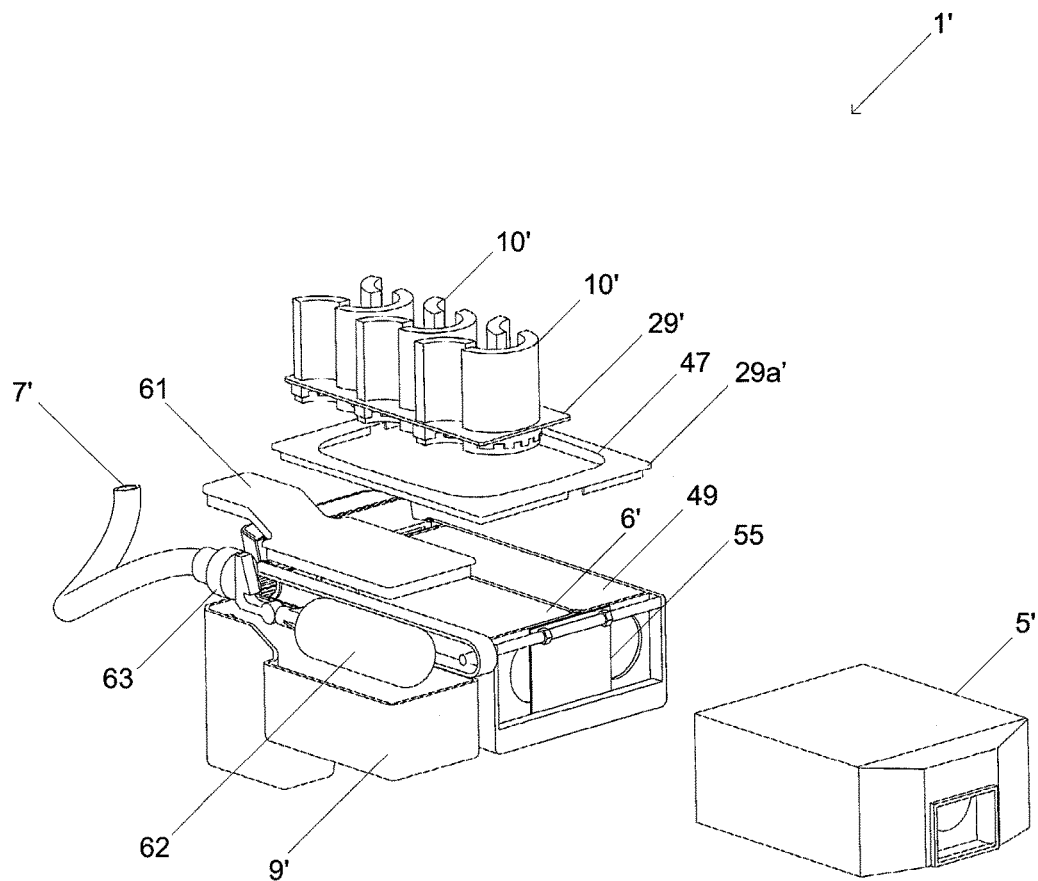
FIG. 11 is an exploded view of a portion of the sterilization and humidification apparatus of FIG. 8.

FIG. 11 shows an exploded view of a part of the sterilization and humidification apparatus 1' of FIG. 8. The figure shows the heating chamber 5', the wicking members 10' (two of which have been indicated), humidification and cooling chamber 6', bypass chamber 49, lid 29*a*' with transparent window 47, and inlet sliding valve 55. The figure shows the wicking members positioned in a barrier 29', which prevents there being a direct interface between the reservoir 9' and humidification and cooling chamber.

FIG. 11 also shows a reservoir 9', reservoir lid 61 and float 62. The reservoir extends beneath the humidification and cooling chamber 6' such that the portion of the wicking members 10' below the barrier 29' are exposed to the water in the reservoir. The float is adapted to ensure the water level in the reservoir is sufficient. When the water level falls (due to water being evaporated in the humidification and cooling chamber), the float will lower. This will open a valve 63 that connects the reservoir to the water source 7'. Water will flow from the water source into the reservoir so that water level rises until the float is at a sufficient level to close the valve.

Figure 12:
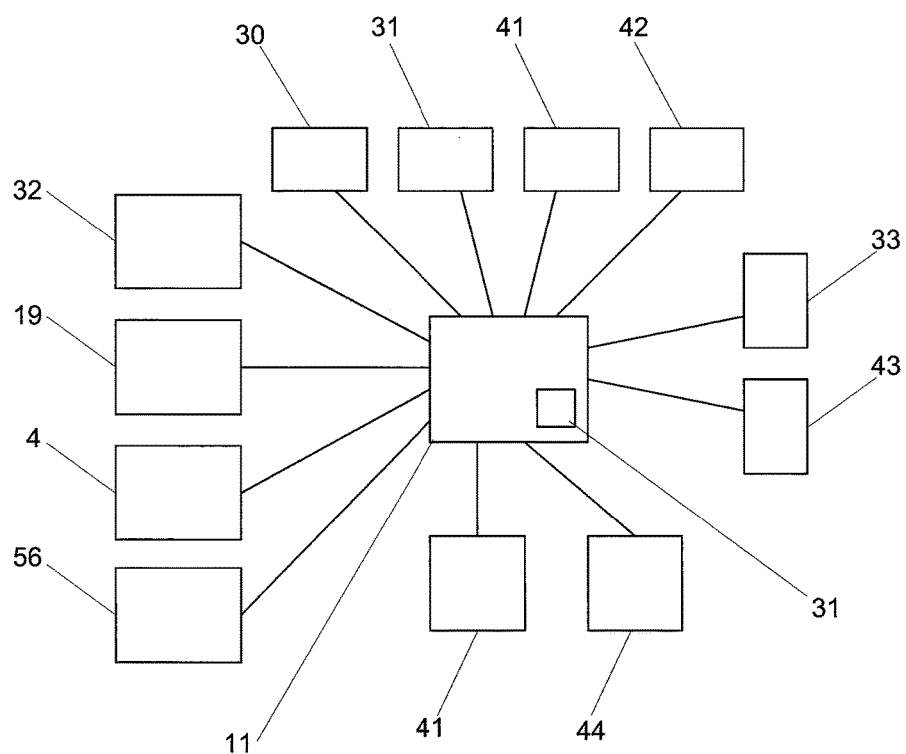
FIG. 12 is a block diagram of a controller.

FIG. 12 shows a block diagram of a controller 11 according to an embodiment of the present invention. The controller is adapted to control the flow device 4, the heater element 19, and the distribution adjustment mechanism (via the drive mechanism 56). The controller is also connected to sensors 30, for detecting various operating states of the sterilization and humidification apparatus. The controller includes a central processing unit 31. In one embodiment, the controller is a digital programmable logic controller.

The controller 11 may control the flow device 4. The controller may control the flow device's on and off cycles or the flow device's speed (that is, where the flow device can achieve a variable flow speed). The controller may control the power input into the flow device or some other operating characteristic of the flow device itself.

Similarly, the controller 11 may control the heater element 19 (and thus the heating chamber). The controller may control the heater element's on and off cycles or the heater element's power or temperature (that is, where the heater element can achieve variable heating). The controller may control the power input into the heater element or some other operating characteristic of the heater element itself.

The controller 11 may control the drive mechanism 56 (and thus the distribution adjustment mechanism 51). Where the drive mechanism is a stepper motor connected to a sliding valve(s), the controller may control the position of the stepper motor, or may turn the stepper motor in an appropriate direction, to control the position of the sliding valve(s).

One or more sensors 30 may be positioned so as to take readings of various parameters at appropriate points in the sterilization and humidification apparatus. Such sensors may be any suitable sensor adapted for measuring the particular parameter, and the invention is not limited in this respect. The measurements could include:

temperature of water source;
temperature of air source;
temperature of air at points within the heating chamber;
temperature of the heater element;
temperature of the bulk conductive material;
temperature of air at points within the humidification and cooling chamber;
temperature of air as it exits the humidification and cooling chamber;
temperature of air at points within the bypass chamber;
temperature of air as it exits the bypass chamber;
humidity of air source;
humidity of air at points within the heating chamber;
humidity of air at points within the humidification and cooling chamber;
humidity of air as it exits the humidification and cooling chamber; and
speed of air flow throughout the sterilization and humidification apparatus.

The readings from these sensors are provided as inputs into the controller, and used by the controller to determine the appropriate operating parameters for the flow device, the heater element and the drive mechanism. The controller may adjust the operating parameters such that the humidified air that exits the sterilization and humidification apparatus has the desired temperature and desired humidity. In one embodiment these are preferably between 25-38 degrees Celsius and 30-80% relative humidity.

The controller may also control other operating parameters of the sterilization and humidification apparatus. The controller may receive input from other sensors 31 as required, and may control other components 32 associated with the sterilization and humidification apparatus as required. For example, these may include:

a clock for recording the running time of an associated incubator; and
alarms for alerting to: the temperature and/or humidity falling outside a desired range; sensor failure; and low water in the water tank or water reservoir.

One or more user input devices 33 may be provided, allowing a user to set control parameters or otherwise interact with the controller. Control parameters may be stored in memory within or associated with the controller.

Thus it will be seen that the sterilization and humidification apparatus is adapted to produce humidified air, with a desired temperature and humidity. In addition, the prior filtration and sterilization of air, and the prior filtration and sterilization of the water, ensures that the humidified air is also filtered and sterilized. Such sterilized and humidified air may be suitable for any number of applications, in particular for use in an incubator.

Figure 13:
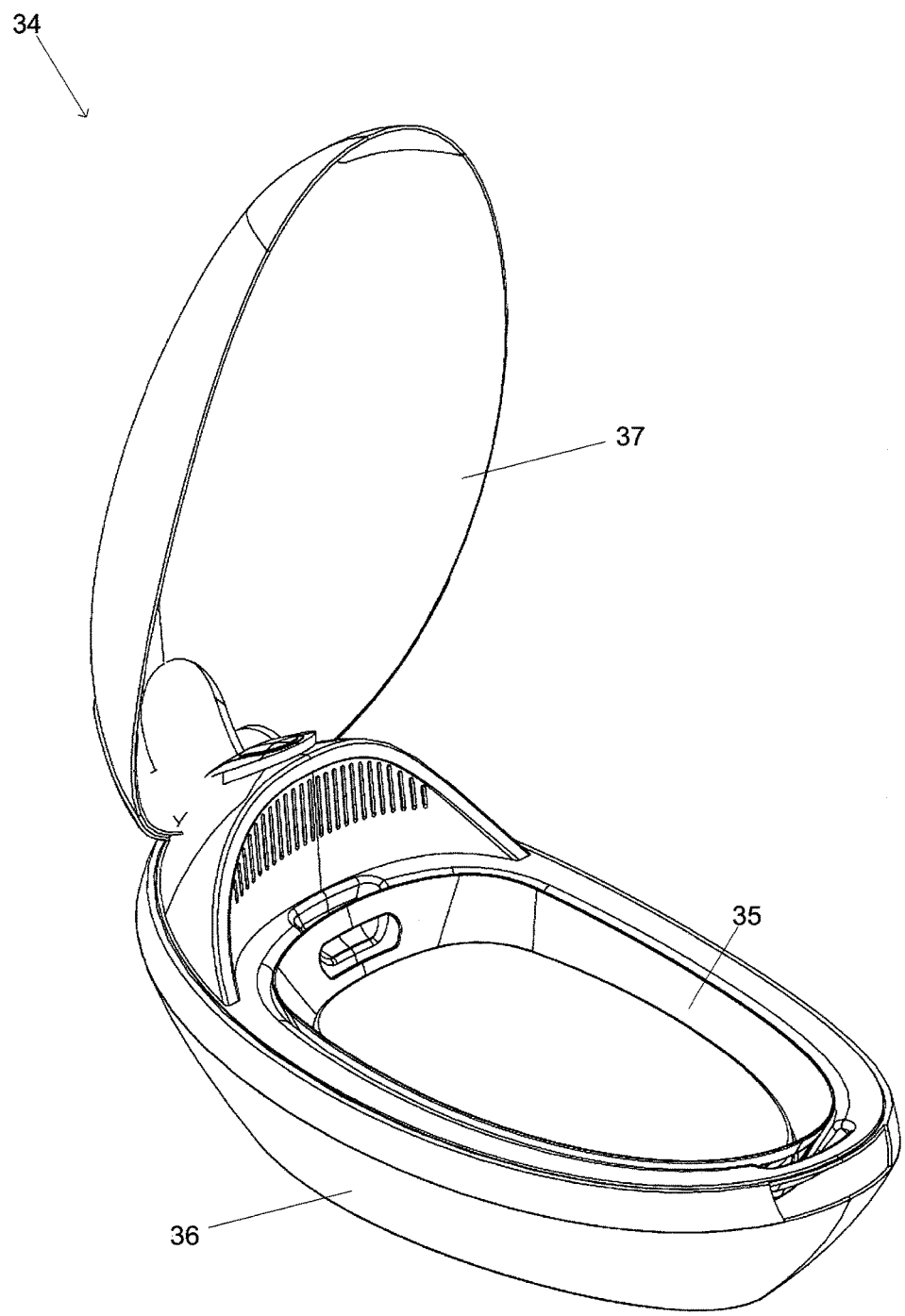
FIG. 13 is an isometric view of an incubator.

FIG. 13 shows an incubator according to an embodiment of the present invention. The incubator 34 includes an occupancy chamber 35 and a bottom section 36. The occupancy chamber includes a top wall 37, which may be hinged or removable enabling access to the interior of the occupancy chamber. In FIG. 13, the top wall is shown in an open position.

In one embodiment of the invention, the occupancy chamber is configured to receive an occupant, generally a human baby. Babies requiring incubation are usually neonatal and/or premature babies. The top wall 37 may be transparent to enable the occupant of the incubator to be visible. To maintain a healthy environment for the occupant of the incubator it is necessary to provide a continuous supply of fresh air. If the air is continuously re-circulated or allowed to stagnate, carbon dioxide and ammonia gas (due to urine exudates) within the incubator may increase to toxic levels.

Figure 14:
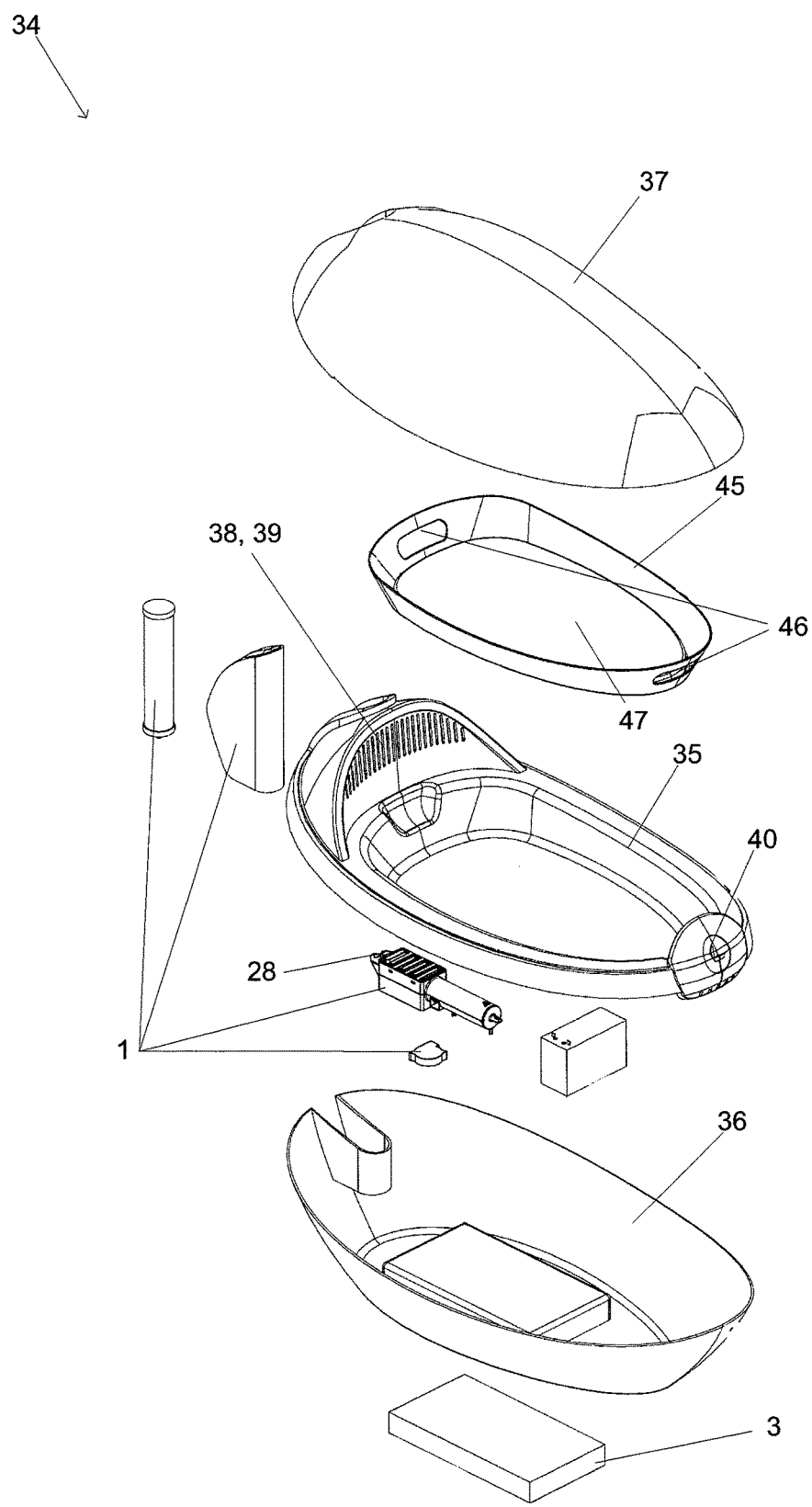
FIG. 14 is an exploded view of an incubator.

FIG. 14 shows an exploded view of the same incubator 34 as that shown in FIG. 13. The incubator includes an occupancy chamber 35, a bottom section 36 and a top wall 37.

The bottom section 36 includes the sterilization and humidification apparatus 1 according to the above description of FIGS. 2-7. The incubator 34 is configured such that the output 28 of the sterilization and humidification apparatus is connected to the occupancy chamber 35 by a suitable conduit. Those skilled in the art will appreciate that the sterilization and humidification apparatus of FIGS. 8 and 9 may alternatively be used.

The humidified air (or mixed humidified air) produced by the sterilization and humidification apparatus 1 then passes into the occupancy chamber 35 through an inlet 38. In on embodiment of the invention, this inlet includes grills 39 that may be designed to create a laminar flow effect. The humidified air passes through the occupancy chamber and is discharged to the ambient environment via a suitable outlet 40. The position of the inlet and the outlet may be configured to promote the flow and cycling of the humidified air in the occupancy chamber. In addition, the geometry of the occupancy chamber may be arranged to promote the flow of the humidified air through the occupancy chamber.

In one embodiment of the invention, when the top wall 37 is opened, the laminar flow of humidified air will continue to pass over the occupant's head and torso, acting as an "air shield".

The incubator 34 may include a controller (not shown). In a preferred embodiment, this controller includes, or is one and the same as, the controller 11 described above in relation to the sterilization and humidification apparatus. Thus, in addition to controlling the operation of the sterilization and humidification apparatus 1, the controller may control the operation of the incubator more generally.

Referring again to FIG. 12, the controller 11 may be connected to further sensors 41 associated with the incubator. These sensors 41 could include sensors for measuring the temperature of the occupant; the temperature of the air inside the occupancy chamber; and the humidity of the air inside the occupancy chamber. The readings from these sensors are provided as inputs into the controller, and used by the controller to determine the appropriate operating parameters for the flow device 4 the heater element 19 and the drive mechanism 56. In a preferred embodiment, the controller controls the sterilization and humidification apparatus to ensure the temperature and humidity inside the occupancy chamber are within desired ranges since this provides the best control of the occupant's immediate environment. In one embodiment, these are preferably between 25-38 degrees Celsius and 30-80% relative humidity.

The controller 11 may record measurements from the various monitoring devices 42. These monitoring devices could include devices for monitoring an occupant's temperature, pulse or respiration rate. The monitoring devices may be hard wired or wireless.

The incubator may include one or more communication ports configured for connection to one or more external devices 43. Information may be communicated from the controller to an external device over any suitable communications link, eg RS-232, USB or a wireless link. Measurements may include temperature inside the incubator, humidity inside the incubator, body temperature of the incubator occupant, and/or any other desired measurement.

One or more display devices 44 may also be provided, for display of operational parameters, alerts, monitoring information, occupant status information (eg temperature, humidity, pulse rate readings etc) or any other required information. A display device may be attached to the side of the incubator.

In one embodiment, the temperature of the occupancy chamber is set by a user, the user being able to set the required temperature or temperature range on the temperature controller.

Referring again to FIG. 13, the occupancy chamber 35 may include a base unit 45 that is formed as a separate, portable unit. The occupant may be disposed on the base unit. This allows the base unit and its occupant to be moved independently of the remainder of the incubator 34. The base unit may be provided with carrying handles 46. The base unit may be fitted with a suitable mattress 47. The mattress may be a removable washable moulded mattress, and may be constructed of a synthetic fibre and wool blend. The mattress may be impregnated with nanoparticulate silver and/or gold, which may provide anti-microbial properties.

The base unit 45 allows measurements or tests (eg weighing the baby) to be performed without unduly disturbing the baby. The weight of the unoccupied base unit is known and can be subtracted from the weight of the base unit and occupant. Other measurements, tests and procedures may also be performed without removing the baby from the portable base unit (eg x-rays, phototherapy).

The occupancy chamber 35 may have suitable openings to allow connection of necessary equipment, such as respirators, IV infusion systems, monitoring equipment and waste systems.

In one embodiment of the invention, the incubator 34 and/or its component parts are made from light, durable materials that can be moulded into the desired components. A preferred material is polypropylene, though a wide number of suitable materials are available, including polyethylene, Perspex, polycarbonate, fibreglass, glass, reinforced plastic, carbon fibre, aluminium and stainless steel.

In one embodiment, at least one interior surface of the incubator 34, preferably an interior wall of the occupancy chamber 35 is coated or impregnated with nanoparticulate silver. This assists with maintaining a relatively sterile chamber as silver in this form has anti-microbial properties.

Although described with reference to a sterilization and humidification apparatus, in one embodiment an incubator may include the humidification device or chamber 6 with or without the heat chamber 5.

Although described in the context of an incubator, the Applicant's sterilization and humidification apparatus has wider applications, particularly in the medical field. The sterilization and humidification device could be used in respiratory humidifiers and/or ventilators or in sterilization systems for medical instruments and the like.

While the present invention has been illustrated by the description of the embodiments thereof, and while the embodiments have been described in detail, it is not the intention of the Applicant to restrict or in any way limit the scope of the appended claims to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departure from the spirit or scope of the Applicant's general inventive concept.

What we claim is:

1. An incubator including:
   i. an occupancy chamber;
   ii. a first inlet for receiving an input gas;
   iii. a second inlet for receiving an input liquid;
   iv. a first porous ceramic filter for filtering the input liquid;
   v. a heating chamber for heating the input gas to a temperature sufficient to sterilize the input gas;
   vi. a humidification chamber, in which, in use, the input liquid evaporates into the input gas after the input liquid has passed through the porous ceramic filter, thereby causing the sterilized gas to cool and producing a humidified gas at a desired temperature in the range of 25 to 38 degrees Celsius, which is made to flow into the occupancy chamber; and
   vii. a second filter for filtering the gas, the second filter including a first filter medium and a second filter medium disposed sequentially in the flow of the gas, with the first filter medium being disposed further upstream in the flow of gas than the second filter medium, and being a readily replaceable filter medium.

2. The incubator as claimed in claim 1, wherein the porous ceramic filter includes an evaporative surface, which brings the filtered liquid into contact with the sterilized gas.

3. The incubator as claimed in claim 1, wherein the porous ceramic filter is adapted to draw the filtered liquid from a source to the humidification chamber by means of capillary action.

4. The incubator as claimed in claim 1, wherein the porous ceramic filter has a maximum pore diameter of 0.2 microns.

5. The incubator as claimed in claim 1, including a further liquid filter for filtering the liquid before it is passed into the porous ceramic filter.

6. The incubator as claimed in claim 5, wherein the liquid filter is a porous material that filters the liquid.

7. The incubator as claimed in claim 6, wherein the porous material of the liquid filter is a porous ceramic with a maximum pore diameter of 0.2 microns.

8. The incubator as claimed in claim 1, wherein the flow of gas and liquid is continuous.

9. The incubator as claimed in claim 1, including a bypass chamber, which provides a path for the sterilized gas to bypass the humidification chamber and a distribution adjustment mechanism that is adapted to adjust the proportion of the sterilized gas that passes through the humidification chamber and the proportion of the sterilized gas that passes through the bypass chamber.

10. The incubator as claimed in claim 9, wherein the distribution adjustment mechanism includes an inlet valve configured to obstruct fully and/or partially an inlet to the humidification chamber and/or an inlet to the bypass chamber.

11. The incubator as claimed in claim 9, wherein the distribution adjustment mechanism includes an outlet valve configured to obstruct fully and/or partially an outlet to the humidification chamber and/or an outlet to the bypass chamber.

12. The incubator as claimed in claim 10, wherein the distribution adjustment mechanism includes an outlet valve configured to obstruct fully and or partially an outlet to the humidification chamber and or an outlet to the bypass chamber, and wherein the inlet valve and the outlet valve operate in unison.

13. The incubator as claimed in claim 1, including one or more sensors for sensing one or more of:

a. a temperature of gas in the heating chamber;

b. a temperature of a heater element;

c. a humidity of the humidified gas; and d. a temperature of the humidified gas.

14. The incubator as claimed in claim 13, wherein a controller receives inputs from the one or more sensors, and controls a flow device and/or the heating chamber to regulate the temperature and humidity of the humidified gas.

15. The incubator as claimed in claim 9, including one or more sensors for sensing one or more of:

a. a temperature of gas in the heating chamber;

b. a temperature of a heater element;

c. a humidity of the humidified gas; and d. a temperature of the humidified gas;

and wherein a controller receives inputs from the one or more sensors, and controls the distribution adjustment mechanism to regulate the temperature and humidity of the humidified gas.

16. The incubator as claimed in claim 1, wherein the humidified gas is between 30-85% relative humidity.

17. The incubator as claimed in claim 1, including or configured for connection to one or more monitoring devices, wherein the one or more monitoring devices include one or more of:

a. a temperature sensor configured to sense a temperature in the occupancy chamber;

b. an occupant temperature sensor; and c. a pulse sensor.

18. The incubator as claimed in claim 17, wherein a controller is configured to control the incubator in accordance with readings from the one or more monitoring devices.

\* \* \* \* \*